United States Patent
Patel et al.

(10) Patent No.: US 7,799,746 B2
(45) Date of Patent: *Sep. 21, 2010

(54) BEAUTY WASH PRODUCT BAR COMPOSITIONS DELIVERING ENHANCED VISUAL BENEFITS TO THE SKIN WITH SPECIFIC OPTICAL ATTRIBUTES

(75) Inventors: Rajesh Patel, Naugatuck, CT (US); Jack Polonka, Peekskill, NY (US); Quynh Pham, Murray Hill, NJ (US); Alexander Lips, Edgewater, NJ (US); Prem Chandar, Closter, NJ (US)

(73) Assignee: Unilever Home & Personal Care USA, Division of Conopco, Inc., Greenwich, CT (US)

( * ) Notice: Subject to any disclaimer, the term of this patent is extended or adjusted under 35 U.S.C. 154(b) by 205 days.

This patent is subject to a terminal disclaimer.

(21) Appl. No.: 11/043,315

(22) Filed: Jan. 26, 2005

(65) Prior Publication Data

US 2005/0220738 A1    Oct. 6, 2005

Related U.S. Application Data

(63) Continuation-in-part of application No. 10/997,180, filed on Nov. 24, 2004, now abandoned, which is a continuation-in-part of application No. 10/814,473, filed on Mar. 31, 2004, now abandoned.

(51) Int. Cl.
*A61K 7/00* (2006.01)

(52) U.S. Cl. .............. 510/130; 510/141; 510/152; 510/153; 510/155; 510/424; 510/475

(58) Field of Classification Search ............... None
See application file for complete search history.

(56) References Cited

U.S. PATENT DOCUMENTS

| | | | |
|---|---|---|---|
| 6,759,376 B2 | 7/2004 | Zhang et al. | |
| 6,780,826 B2 * | 8/2004 | Zhang et al. | 510/130 |
| 6,906,015 B1 * | 6/2005 | Shiloach et al. | 510/130 |
| 2004/0186030 A1 * | 9/2004 | Hofrichter et al. | 510/130 |
| 2004/0223993 A1 * | 11/2004 | Clapp et al. | 424/401 |
| 2004/0234470 A1 | 11/2004 | Zhang et al. | |
| 2004/0234565 A1 * | 11/2004 | Stella et al. | 424/401 |

OTHER PUBLICATIONS

Patel et al., U.S. Appl. No. 10/814,473, filed Mar. 31, 2004, Beauty wash product bar compositons delivering enhaced visual benefits to the skin with specific optical attributes, (now abandoned).
Patel et al., U.S. Appl. No. 11/043,315, filed Nov. 24, 2004, Beauty wash product bar compositons delivering enhaced visual benefits to the skin with specific optical attributes.
Polonka et al., U.S. Appl. No. 10/815,003, filed Mar. 31, 2004, Beauty wash product compositions delivering enhaced visual benefits to the skin with specific optical attributes, (now abandoned).
Polonka et al., U.S. Appl. No. 10/996,532, filed Nov. 24, 2004, Beauty wash product compositions delivering enhanced visual benefits to the skin with specific optical attributes.
Polonka et al., U.S. Appl. No. 11/043,509, filed Jan. 26, 2005, Beauty wash product compositions delivering enhanced visual benefits to the skin with specific optical attributes.
Tsaur et al., U.S. Appl. No. 10/814,879, filed Mar. 31, 2004, Rinse-off facial wash compositions delivering enhanced whitening using submicron titanium oxide, optional modifier and deposition system, (now abandoned).
Tsaur et al., U.S. Appl. No. 10/997,179, filed Nov. 24, 2004, Rinse-off facial wash compositions delivering enhanced whitening using submicron titanium oxide, optional modifier and deposition system.

* cited by examiner

*Primary Examiner*—Necholus Ogden, Jr.
(74) *Attorney, Agent, or Firm*—Ronald N. Koatz

(57) ABSTRACT

The present invention relates to beauty wash bar compositions which deliver enhanced visual benefits to the skin with specific optical attributes. This is accomplished using specific deposition systems (where oil/emollient comprises part of deposition system) and/or by ensuring dispersion of particles onto skin.

24 Claims, No Drawings

BEAUTY WASH PRODUCT BAR COMPOSITIONS DELIVERING ENHANCED VISUAL BENEFITS TO THE SKIN WITH SPECIFIC OPTICAL ATTRIBUTES

RELATED APPLICATIONS

The present application is a continuation-in-part of application U.S. Ser. No. 10/997,180 to Patel et al., filed Nov. 24, 2004 Now abandoned (adding additional examples), which in turn is a continuation-in-part of U.S. Ser. No. 10/814,473, filed Mar. 31, 2004 Now abandoned.

FIELD OF THE INVENTION

The present invention relates to compositions delivering solid particulate optical modifiers (e.g., titanium dioxide, mica, etc.) delivering enhanced visual benefits (gloss, shine, color) to the skin using specific deposition systems capable of delivering the optical modifiers from rinse-off bar compositions to provide specific optical attributes (e.g., to enhance reflectance by certain percent and/or to change unit lightness or color values in amounts previously not possible in rinse-off systems). Generally, the enhancement is obtained by use of specific deposition system (e.g., cationic polymer/anionic surfactant precipitates and wherein the deposition system also comprises oil/emollient) and/or by ensuring dispersion of particles (e.g., little or no agglomeration) onto skin or deposited substrate. Bar processing parameters may help enhance this dispersion.

BACKGROUND

It is extremely difficult to deliver enhanced optical properties (radiance; whiteness; perceived blueness versus yellowness or reds versus green) from a rinse-off composition (e.g. liquid or bar compositions). The optical modifiers delivering these properties are not readily deposited, are readily rinsed of and, because they readily agglomerate, are not in a sufficiently dispersed state to be efficiently delivered to substrate (which is another way to say that they rinse off too easily).

Applicants' co-pending U.S. Ser. No. 10/241,401 to Zhang et al., filed Sep. 11, 2002 discloses personal care formulations comprising particles of defined refractive index, thickness, geometry and size. While this disclosure relates to how size, shape, etc. of the particles themselves help deposition (and thus shine), it fails to disclose specific deposition enhancement systems (e.g. based on type of surfactant and/or polymers), and the use of such systems to deliver specifically targeted optical properties when values defining these targeted properties are changed by certain absolute or percentage amounts. It also does not disclose how particles must be adequately dispersed on substrate (e.g., skin) to deliver defined change values needed to perceive measure optical traits.

U.S. Ser. No. 10/443,396 to Zhang et al., filed May 23, 2003 discloses structured benefit agent for enhanced delivery of optical modifier, but again does not disclose specific delivery systems, does not disclose necessity of, or manner to achieve particulate dispersal, and does not disclose compositions or materials needed to deliver change in values (absolute or percentage) associated with perceived optical benefit.

In a related application filed Nov. 24, 2004, applicants claim compositions for delivering of enhanced visual benefits to skin with specific optical attributes. This claim covers optical modifiers combined with deposition enhancement system, but do not specifically claim such deposition system must comprise oil/emollient. The subject application adds some additional examples where oil is present in the deposition system (there are some example in the related application where oil is used, e.g., bismuth oxychloride is commercially sold as solids suspended in oil such as, for example, castor oil) and further specifically claims the bar compositions.

In a co-pending application filed the same date as the subject application, compositions where oil/emollient comprises part of the deposition system are claimed, but the subject invention is directed more specifically to bar compositions.

BRIEF SUMMARY OF THE INVENTION

Applicants have now found both compositions and ways to manipulate such compositions to provide specific optical benefits from bar systems. That is, using deposition enhancement systems (e.g., characterized, for example, by precipitates formed through interaction of polymers and surfactants and the use of oil/emollient in the deposition system), modifiers associated with specified optical properties (gloss, whiteness, degree of "blueness") can be dispersed and delivered to provide desired optical attributes (i.e., by providing sufficient change in absolute or percentage values of the components to result in perceived optical changes). Changes in optical attributes previously unobtainable from wash-off/rinse-off bar systems are provided by selecting the specified components.

More particularly, the invention comprises as follows:

Beauty wash product compositions for delivery of enhanced (changed) visual benefits to the skin with specific optical attributes comprising:

a) from 5.0% to about 75%, preferably 10% to 75%, more preferably 15% to 70% by weight surfactant selected from anionic, nonionic, amphoteric and cationic surfactants and mixtures thereof;

b) from 0.1 to 35%, preferably 0.2 to 25% by weight of solid particulate optical modifier which exhibits a specific set of optical properties (e.g., defining radiance or shine ($\Delta$ gloss), whiteness ($\Delta L$), degree of red or greenness ($\Delta a^*$), degree of yellow or blueness ($\Delta b^*$), change in opacity) and which, in combination with a deposition enhancement system, provides at least 5% improvement (i.e., 5% change) in at least one visual attribute being targeted (e.g., shine, color), wherein values reflecting various optical properties are measured before or after conducting tests according to a defined protocol, when said composition is applied to the skin;

c) from 0.1 to 25% by wt. of a deposition enhancement system, wherein, the deposition enhancement system enhances delivery to the skin of a target or defined visual attribute (e.g. shine) by the optical modifier relative to a composition that has the same surfactant and optical modifier used at the same concentration but does not have the deposition enhancement system; and d) from about 0.1% to 80% of a hydrophillic structural dispersant (for example, polysaccharides such as sugar, xantham gum, agar; alkaloid derived polymers such as starch, cellulose and their soaps; fatty acid soap crystals, polyols, polyalkylene glycol, inert solid phase structuring materials and mixtures thereof);

In a preferred embodiment, the structurant is a hydrophilic structurant such as polyalkylene oxide (e.g., polyethylene glycol) or soluble sugar;

e) 1% to 12% by wt. water.

wherein said deposition enhancement system comprises oil/emollient

As noted, the changes in visual attribute may be measured by a change in value of at least one component (gloss value, color value defined by an a* or b* value) of at least 5% in absolute or percent terms.

These and other aspects, features and advantages will become apparent to those of ordinary skill in the art from a reading of the following detailed description and the appended claims. For the avoidance of doubt, any feature of one aspect of the present invention may be utilized in any other aspect of the invention. It is noted that the examples given in the description below are intended to clarify the invention and are not intended to limit the invention to those examples per se. Other than in the experimental examples, or where otherwise indicated, all numbers expressing quantities of ingredients or reaction conditions used herein are to be understood as modified in all instances b the term "about". Similarly, all percentages are weight/weight percentages of the total composition unless otherwise indicated. Numerical ranges expressed the format "from x to y" are understood to include x and y. When for a specific feature multiple preferred ranges are described in the format "from x to y" it is understood that all ranges combining the different endpoints are also contemplated. Where the term "comprising" is used in the specification or claims, it is not intended to exclude any terms, steps or features not specifically recited. All temperatures are in degrees Celsius (° C.) unless specified otherwise. All measurements are in SI units unless specified otherwise. All documents cited are—in relevant part—incorporated herein by reference.

DETAILED DESCRIPTION OF THE INVENTION

The present invention relates to composition and to methods of delivering enhancement in delivery of a targeted visual value (e.g., reflectance/shine; opacity/translucency; whiteness; blueness; rosiness) from bar compositions. Specifically, by using deposition enhancement systems (specifically, those comprising oil/emollient as part of the deposition enhancement system), the targeted values can be manipulated to deliver the desired attribute or look.

Specifically, the rinse-off compositions of the invention comprise:

a) 5.0% to 75%, preferably 10% to 70%, more preferably 15 to 70%, even more preferably 20 to 70% by wt. of a surfactant or mixture of surfactants;

b) 0.1% to 35%, preferably 0.2% to 25% by wt. of a solid particulate optical modifier enhancing a specific set of properties (e.g. whiteness) and which, in combination with deposition enhancement system for the modifier (e.g. precipitate formed from interaction of polymer and surfactant) provides at least 5% change in at least one targeted visual attribute, wherein said change is defined by increase or decrease in absolute or percentage value characterizing a specific trait (i.e., Δ gloss is associated with radiance or ΔL with whiteness) and evaluation is made after using a defined in vitro skin protocol test;

c) from 0.1 to 25% by wt. of said deposition enhancement system wherein, said system (c) is defined by its ability to enhance delivery of said targeted visual attribute, by the modifier relative to composition with some surfactant and modifier at same concentration, but which does not have the deposition enhancement system, and d) from 0.1 to 80% by wt. of a hydrophilic structural dispersant; and e) 1% to 12% by wt. water;

wherein said deposition enhancement system comprises oil/emollient as part of the system.

In general, the surfactant system used is also not critical. It is, however, preferred that there be present at least one lathering anionic surfactant.

Surfactant is present at a level of 5.0 to 75%, preferably 10 to 70%, more preferably 15 to 70% by wt. of composition.

In general, as noted, the surfactant may be selected from the group consisting of soap (including pure soap systems), anionic surfactant, nonionic surfactant, amphoteric/zwitterionic surfactant, cationic surfactant and mixtures thereof.

Preferably, the surfactant should be a lathering in surfactant which will allow the composition to lather at least 30 cc in a lather test.

"Soap" is used is in the popular sense i.e., alkali metal or alkanol ammonium salts of aliphatic, alkane or alkene monocarboxylic acids. Other surfactants which may be used are described in "Surface Active Agents and Detergents" (Vol. I & II) by Schwartz, Perry & Berch, a copy of which is incorporated by reference into the subject application.

Bars may include pure soap bars, bars which are primarily (>50% of surfactant system) soap and have some synthetic, bars which are primarily synthetic and have some soap, bars which are primarily sugar based bars, bars which are primarily polyethylene glycol based bars, etc.

With regard to visual attributes targeted by the optical modifier, these attributes may include, but are not limited to, attributes such as skin shine, skin lightness, skin color, skin glow, skin radiance, skin optical uniformity, skin evenness, and combinations thereof.

As indicated, the particulate optical modifier should change provide, in combination with deposition enhancement system, at least a 5% change in a visual attribute being targeted, wherein 5% increase refers to of at least one of various values (L, a*, b* gloss, etc.) which is associated with a particular attribute identified with the value (e.g.; L refers to "whiteness").

Specifically, improvement is measured by taking a value for a particular measured component (for example, gloss value, L value, a* value, b* value) and measuring (e.g. using in in vitro pig assay) values of these components before and after application of particle deposition enhancement system.

Thus, for example, if gloss score changes from 5.5 to 7.8 (or visa versa) (as measured in a gloss meter), there is a percent differential of 41.8% in gloss. Similarly, if "a*" value (measure of rosiness) goes from 2.3 to 0.8, this is an absolute decrease of −1.5, well beyond 5%.

The optical benefit carried by the deposition of optical modifier can be targeted to either plateaus on the skin surface or to skin crevices.

In one embodiment of the invention, in absolute value, the composition of the invention (with modifier and added deposition system relative to composition with no deposition system) deposits modifier to exhibit ΔL value in range of 0 to ±10 "L" units, wherein said L units are defined by Hunter Lab Color Meter as described in the protocol, reflectance change in range of 0 to about ±300% as defined by a change in measured gloss from a gloss meter; and change in opacity in range from about 0 to ±50% measured in opacity contrast defined as ΔL divided by 60; wherein, at least one value has a change of at least 5% from the initial value prior to delivery of modifier.

In another embodiment, the formulation deposition of modifier creates a change in skin shine, glow or similar attributes, and the particulate optical modifier deposits to exhibit ΔL value in range of about 0 to about ±10 L units, reflectance change in the range from 0 to about ±300% change in gloss, and a change in opacity in a range of 0±20%, wherein, Δa* and Δb* are within normal skin range. Maintaining a normal skin range means that Δa* and Δb* are <2 Δa* or Δb* units, respectively, preferably less than 1 unit. Again, there must be a least 5% change in at least one of reflectance, L, or opacity.

In another embodiment, the formulation deposition of modifier creates skin lightening, whitening, and/or color or similar attributes and the composition deposits particulate optical modifier to exhibit ΔL value in the range of ±10 L units, Δa* value in range from about 0 to about ±10, Δb* value in range from about 0 to about ±10, and a change in opacity in the range from about 0 to about ±50%. The reflectance is within normal skin reflectancy range. In this case, this means change in reflectance is ≦10%. Here, as noted, there is more of a focus on Δa* and Δb* values since there is a focus on general color attributes.

In yet another embodiment, the formulation creates skin optical uniformity, evenness, blurring, soft focus or similar attributes and the composition deposits particulate optical modifier to exhibit ΔL value in the range of ±5 L units, a reflectance change in the range from about 0 to about ±100% (gloss units) and a change in the opacity in the range from about 0 to about ±50% (defined by ΔL/60), wherein Δa* and Δb* are within normal skin color range. (change of ≦2 a* or b* units respectively).

What is important to note is that the formulation can be formulated to yield a mixture (one or more effects/visual attributes) depending on the exact mixture of particles and/or particle types and/or deposition enhancement. Obtaining specific visual attributes of this kind by manipulating L or a* or b* or gloss value has not been previously possible from a wash-off system.

Specifically, any individual visual effect can be obtained by adjusting the optical space to specifically desired optical space within ranges of, for example, ΔL, Δa*, Δb*, etc. It should be noted, if not already clear, that ranges can be manipulated to obtain effect for one or more attributes or mixtures thereof.

Structurant

The structurant of the invention can be a water-soluble or water insoluble structurant.

Water soluble structurants include moderately high molecular weight polyalkylene oxides of appropriate melting point (e.g. 40° to 100° C., preferably 50° to 90° C.) and in particular polyethylene glycols or mixtures thereof.

Polyethylene glycols (PEG's) which are used may have a molecular weight in the range 2,000 to 25,000 preferably 3,000 to 10,000. However, in some embodiments of this invention it is preferred to include a fairly small quantity of polyethylene glycol with a molecular weight in the range from 50,000 to 500,000, especially molecular weights of around 100,000. Such polyethylene glycols have been found to improve the wear rate of the bars. It is believed that this is because their long polymer chains remain entangled even when the bar composition is wetted during use.

If such high molecular weight polyethylene glycols (or any other water soluble high molecular weight polyalkylene oxides) are used, the quantity is preferably from 1% to 5%, more preferably from 1% or 1.5% to 4% or 4.5% by weight of the composition. These materials will generally be used jointly with a large quantity of other water-soluble structurant such as the above mentioned polyethylene glycol of molecular weight 2,000 to 25,000, preferably 3,000 to 10,000.

Water insoluble structurants also have a melting point in the range 40° to 100° C., more preferably at least 50° C., notably 50° C. to 90° C. Suitable materials which are particularly envisage are fatty acids, particularly those having a carbon chain of 12 to 24 carbon atoms. Examples are lauric, myristic, palmitic, stearic, arachidic and behenic acids and mixtures thereof. Sources of these fatty acids are coconut, topped coconut, palm, palm kernel, babassu and tallow fatty acids and partially or fully hardened fatty acids or distilled fatty acids. Other suitable water insoluble structurants include alkenols of 8 to 20 carbon atoms, particularly cetyl alcohol. These materials generally have a water solubility of less than 5 g/litre at 20° C.

Soaps (e.g. sodium stearate) can also be used at levels of about 1% to 15%. The soaps may be added neat or made in situ by adding a base, e.g. NaOH to convert free fatty acids.

The relative proportions of the water-soluble structurants and water insoluble structurants govern the rate at which the bar wears during use. The presence of the water-insoluble structurant tends to delay dissolution of the bar when exposed to water during use and hence retard the rate of wear.

The structurant is used in the bar in an amount of 20% to 85%, preferably 30% to 70% by wt.

In a preferred embodiment, the surfactant comprises predominantly water-soluble structurant. Hydrophobic structurant (e.g., free fatty acids, waxe) should comprise no more than 255, preferably no more than 10% of structurant system; and such hydrophobic structurant should comprise no more than 25%, preferably also than 20%; more preferably less than 15% by wt. of bar overall.

By water soluble is meant generally that 1% or more of compound is soluble in water at room temperature.

Optical Modifier

The optical modifier which may be used for the subject invention may be chosen from non-colored and colored, organic and inorganic materials.

Among the materials which may be used are included:

Organic pigments, inorganic pigments, polymers and fillers such as titanium oxide, zinc oxide, colored iron oxide, chromium oxide/hydroxide/hydrate, alumina, silica, zirconia, barium sulfate, silicates, natural/alkaloid (including derivatives) polymers, polyethylene, polypropylene, nylon, ultramarine, alkaline earth carbonates. The materials can be platy materials such as talc, sericite, mica, synthetic mica, platy substrate coated with organic and inorganic molecules, bismuth oxychloride, barium sulfate. Particle can be composed of several materials (like dyes, lakes, toners). Lakes are, for example, dyes with aluminum hydroxide to help bind to solid. Color can be generated through fluorescence, absorption or iridescence. That is, color of modifier materials is generated through optical means rather than, for example, chemical means.

The optical modifier may also be a UV screen material with a $D_{50}$<100 nanometers (where $D_{50}$ means size of 50% of particles or less is <100→m.

The optical modifiers may also be defined by their physical properties. For example, the optical modifier may be broadly defined as follows:

i) an exterior surface having a refractive index of 1.3 to 4.0;

ii) a geometry which is spheroidal, platy or cylindrical;

iii) dimensions: spheroidal −0.1 to 200 µm, platy −1 to 200 µm, cylindrical −1 to 200 µm in length and 0.5 to 5.0 µm in diameter;
iv) a D50 of ≦200 microns in particle size; and
v) may have fluorescence color, absorption color and/or interference color (color through optics).

More specifically particles providing change in shine/glow/radiance may be defined as follows:
i) an exterior surface having a refractive index of 1.8 to 4.0;
ii) a geometry which is platy or cylindrical;
iii) dimensions: spheroidal −0.1 to 200 µm (microns) platy −10 to 200 µm, cylindrical −10 to 200 µm in length and 0.5 to 5.0 µm in diameter; and
iv) a $D_{50}$ of ≦200 µm in particle size.

Particle providing skin lightening/color may be defined as follows:
i) an exterior surface having a refractive index of 1.3 to 4.0;
ii) a geometry which is spheroidal or platy;
iii) dimensions: spheroidal −0.1 to 1 µm, platy −1 to 30 µm;
iv) a $D_{50}$ Of ≦300 µm, in particle size; and
v) may have fluorescence color, absorption color and/or interference color (color through optics).

Particle-producing evenness or soft focus may be defined as follows:
i) an exterior surface having a refractive index of 1.3 to 2.0;
ii) a geometry which is spheroidal, platy or cylindrical;
iii) dimensions: spheroidal −0.1 to 200 µm, platy −1 to 10 µm, cylindrical −1 to 10 µm in length and 0.5 to 5.0 µm in diameter; and
iv) a $D_{50}$ of ≦200 µm in particle size.

Of course, the formulation can contain a mixture of particles, each containing characteristics of a specific visual benefit, to create a combination of visual effects.

It is also to be understood that for visual effects/attributes to have maximum effect, the particles have to be well dispersed on the skin and should also give minimal to no sensory negatives.

By being "well dispersed" is meant that the particles should not agglomerate and that they should be spread easily through the skin surface.

In a preferred embodiment, less than 30% of particles are agglomerates having a size of ten times or more than the $D_{50}$ particles size. This can be measured using optical or electron microscopy.

The particle is used at about 0.1% to 35% by weight preferably 0.2 to 25% by wt. of the composition.

Deposition Enhancement

The deposition enhancement is key to the delivery of particles providing enhanced visual benefit (e.g., as defined in changes in) L,) a*, etc. and in methods to manipulate the values to provide the desired benefit, e.g. radiance, color, etc.).

In one embodiment, the deposition is provided by a deposition system comprising as follows:
a) from about 0.1 to about 10% by wt., preferably 0.1 to 8% by wt. of a cationic polymer having change density ≧1 Meq/gram, and
b) about 0.1 to 30% by wt., preferably 0.5 to 25% by wt. of an anionic surfactant which forms a precipitate with cationic polymer upon dilution
c) 0.1 to 40% oil/emollient which comprises part of the deposition enhancement system.

The precipitate formed can be a floc which can be broken up upon shear or rubbing to form a uniform and dispersed film on the surface of the skin.

Example of such surfactants include $C_{10}$-$C_{24}$ fatty acid soaps (e.g., laurates), alkyl taurate (e.g., cocoyl methyl taurate or other alkyl taurates), sulfosuccinates, alkyl sulfates, glycinates, sarcosinates and mixtures thereof.

It is important that the cationic have the noted charge in order to form the precipitate which is a key to the deposition of optical modifiers delivering the desired optical attributes. The polymers may be modified polysaccharides including cationic guar gums, synthetic cationic polymers, cationic starches, etc.

Specific cationic polymers which are to be used include Merquat® polymers such as polyquaternium 6 (e.g., Merquat®100 or Salcare®SC30) and polyquatrnium 7 (e.g. Merquat®2200 or Salcare®SC10); guar gums and/or derivatives (e.g. Jaguar C17); quaternized vinylpyrrolidone/methacrylate copolymers (e.g., Gafquat® 775); and polyquaternium-16 (e.g.; Luviquat®FC550).

Specific examples of polymers and their charge densities are disclosed in the Table below:

| Type of Polymer | TradeName | Company | Charge Density (meg/g) |
|---|---|---|---|
| Guar | | | |
| Guar hydroxypropyltrimonium chloride | Jaguar C17 | Rhodia | >Jaguar C13S |
| Hydroxypropyl guar hydroxypropyltrimonium chloride | Jaguar 162 | Rhodia | −Jaguar C13S |
| Guar hydroxypropyltrimonium chloride | Jaguar C13S | Rhodia | 0.8 |
| Guar hydroxypropyltrimonium chloride | Jaguar C14S | Rhodia | ~Jaguar C13S |
| Guar hydroxypropyltrimonium chloride | Jaguar Excel | Rhodia | ~Jaguar C13S |
| Guar hydroxypropyltrimonium chloride | N-Hance 3000 | Hercules | 0.41 |
| Guar hydroxypropyltrimonium chloride | N-Hance 3196 | Hercules | 0.72 |
| Guar hydroxypropyltrimonium chloride | N-Hance 3215 | Hercules | 1.05 |
| Synthetics | | | |
| Polyquaternium-6 | Merquat 100 | Ondeo Nalco | 6.2 |
| Polyquaternium-7 | Merquat 2200 | Ondeo Nalco | 3.1 |
| Polyquaternium-7 | Merquat 550 | Ondeo Nalco | 3.1 |
| Polyquaternium-7 | Merquat S | Ondeo Nalco | 3.1 |
| Polyquaternium-7 | Salcare Super 7 | Ciba | 1.5 |
| Polyquaternium-7 | SalcareSC10 | Ciba | 4.3 |
| Polyquaternium-7 | Salcare SC11 | Ciba | 3.1 |

-continued

| Type of Polymer | TradeName | Company | Charge Density (meg/g) |
|---|---|---|---|
| Polyquaternium-6 | Salcare SC30 | Ciba | 6.2 |
| Polyquaterniumj-16 | Luviquat FC370 | BASF | 2 |
| Polyquaterniumj-16 | Luviquat FC550 | BASF | 3.3 |
| Polyquaterniumj-16 | Luviquat FC552 | BASF | 3 |
| Polyquaterniumj-16 | Luviquat FC905 | BASF | 6.1 |
| Polyquaternium-44 | Luviquat MS370 | BASF | 1.4 |
| Cationic Cellulose Derivatives | | | |
| Polyquaternium-4 | Celquat H-100 | National Starch | 0.71 |
| Polyquaternium-4 | Celquat L-200 | National Starch | 1.43 |
| Polyquaternium-4 | Celquat SC230M | National Starch | 1.36 |
| Polyquaternium-4 | Celquat SC240C | National Starch | 1.29 |
| Polyquaternium-4 | UCARE Polymer JR | Dow Amerchol | 1.3 |
| Polyquaternium-4 | UCARE Polymer JR | Dow Amerchol | 0.7 |
| Dextran Derivatives | | | |
| Dextran hydroxypropylammonium chloride | CDC | Meito Sangyo | 1.6 |

The oil/emollient which comprises part of deposition system can be, for example, silicone, castor oil, sunflower seed oil. Preferably, by comprising part of the deposition system is meant that the deposited particle may be enveloped/surrounded by the oil and/or be part of an emulsion system in which deposited particles are emulsified in the oil/emollient, or becomes enveloped/surrounded during dilution with water.

One example of such particles suspended in oil, for example, is bismuth oxychloride suspended in castor oil (e.g., Rona® Biron Silver, a 70% solids suspension in castor oil). Such solution was used in the part application of the subject application filed Nov. 24, 2004 (see, for example, Formulation 6 or 7) as well as in the grandparent application, filed Mar. 31, 2004.

In general, other deposition aids (e.g., for the optical modifier particles) may include granular anionic polymers (e.g. alkaloid polymer such as starch, cellulose or their derivatives). That is, if the deposition system additionally comprises such deposition aid, results are further enhanced. Incorporation of the emollient as part of the deposition system as noted above boosts the deposition system. The enhancement would be for example, at least 10% in some value (e.g., gloss $\Delta L$, $\Delta a^*$ or $\Delta b^*$) relative to if no emollient is added to the deposition system at all.

It should be further noted that oils/emollients may be used which are not specifically associated with deposition and which are added for sensory (e.g., tactile) effect. Among oils which may be used are included, for example, vegetable oils such as orachis oil, castor oil, cocoa butter, coconut oil, corn oil, cotton seed oil, palm kernel oil, rapeseed oil, sunflower seed oil, safflower seed oil, sesame seed oil and soybean oil.

Emollients may include the vegetable oils noted above and may further comprise esters, fatty acids, alcohols, polyols and hydrocarbons. Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate.

Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate and co-caprate, propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol.

Yet, another way to enhance deposition may be through modification (e.g. surface modification) of particles.

In another embodiment, the deposition enhancement system may comprise:

1) from 0.1 to 10% by wt. of an anionic polymer having charge density of at least $\geq 1.0$ Meq/gram; and
2) from about 0.1 to 30% cationic surfactant which forms a precipitate with the anionic polymer upon dilution;
3) 0.1 to 40.0% by wt. oil/emollient.

This system is the inverse of cationic polymer anionic surfactant system. The precipitate can also be a floc which can be broken up on shear or rubbing and form a uniform and dispersed film on the skin surface.

Cationic surfactant may be a quaternary amino surfactant or an amphoteric such as betaine (e.g., cocoamidopropyl betaine).

The anionic polymer may be a polyacrylate, cross-linked polyacrylate, polyurethane and/or alkaloid derived polymer (e.g., starch, cellulose and derivatives), polysaccharide (e.g. xanthan gum), agar and/or mixtures thereof.

This system may also additionally comprise 0.1 to 30% granular anionic polymer which is natural alkaloid polymer (starch, cellulose and derivatives) as deposition aid.

EXAMPLES

Protocol

In Vitro Porcine/Pig Skin Assay

A piece of black porcine skin is used (L=40±3), where skin has dimensions of 5.0 cm by 10 cm, and the skin is mounted on black background paper card. Initial measurements of untreated skin are made. The mounted skin is then washed and rinsed with 0.2 g of liquid wash-off formulation or soap bar. After two (2) hours of drying, final measurements are made.

Color Measurements

Initial and final color measurements were made of porcine or in-vivo human skin using a Hunter Lab spectra colormeter using a 0° light source and 45° detector geometry. The spectra colormeter was calibrated with the appropriately black and white standards. Measurements were made before and after wash treatment. Three measurements were made each time and averaged. Values of L, a*, and b*, which came from the L a* b* color space representation, were obtained in this manner. L measures units of "Lightness", a* measures values from red to green and b* measures values from yellow to blue.

Reflectance (Gloss) Determination

Initial and final reflectance/radiance measurements of porcine or in-vivo human skin was made with a glossmeter which measures units of gloss. The glossmeter was first set with both detector and light source at 85° from normal. The glossmeter was calibrated with appropriate reflection standard. Measurements of gloss were taken before and after application of formulation and Δ gloss was calculated to obtain percent difference.

Opacity Determination

Opacity of washable deposition was calculated from Hunter Lab color measurements. Opacity contrast was calculated from ΔL (change in whiteness after deposition compared to prior to deposition) divided by 60 (which is the difference in L value of skin and a pure white color).

Stop

Example for Bars

Formulations for Bar referred to as Formulation 1 to 7 are set forth below.

Formulation 1:

60% Talc in pure soap bar, wherein soap is a mixture of 15-20% coconut oil and 80 to 85% tallow. Typically, such a mixture has about 95% $C_{12}$ to $C_{18}$ fatty acids Formulation 2:

| Ingredient | % by weight |
|---|---|
| Polyethylene glycol - 8K | 43.5% |
| Cocoamidosulfosuccinate | 30% |
| Fatty Acid | 10% |
| Sunflower Seed Oil | 10% |
| Merquat ® cationic | 1.5% |
| Water | 5% |
| TiO$_2$ | 16% |

In formulation 2, the cocoamidosulfosuccinate and Merquat are primary deposition aids. The sunflower seed oil is believed to be sensory, but not to significantly enhance deposition (see % gloss figures of −45.1 and −44.6 in Table). Further, TiO$_2$ is not an oil emulsion so no further deposition enhancement is seen from oil being part of the deposition system.

Formulation 3:

| Ingredient | Ingredient |
|---|---|
| Sugar (e.g., sucrose) | 45% |
| Maltodextrin | 15% |
| Sodium Laurate | 15% |
| Sodium dodecyl sulfate | 2% |
| Merquat ® cationic | 0.4% |
| TiO$_2$ | 10% |
| H$_2$O | to balance |

Similar to Example 2, cationic and anionic surfactant provide most or all deposition enhancement and TiO$_2$ adds little to deposition.

Formulation 4—same as Formulation 2, but with 10% TiO$_2$ coated with mica instead of TiO$_2$.

As seen, mica coating enhances reflectance and whiteness.

Formulation 5—same as Formulation 3, but with 10% TiO$_2$ coated with mica instead of TiO$_2$.

Formulation 6—same as Formulation 2, but with 10% bismuth oxychloride (Rona Biron Silver, a 70% solids suspension is castor oil) instead of TiO$_2$.

In this formulation, the oil (castor oil emulsion of bismuth oxychloride) is part of the deposition system. Comparing Formulation 6 to 2 (Examples 23 and 24 to 15 and 16), it can be seen deposition (and % gloss) is significantly enhanced.

Formulation 7—same as Formulation 3, but with 10% bismuth oxychloride instead of TiO$_2$.

Similar to Formulation 6 relative to 2, when bismuth emulsified in oil (as part of deposition system) is used (see 26 and 27 versus 17 and 18), deposition (reflected in % gloss) is significantly enhanced.

Formulation 8—same as Formulation 5, but with 2% sodium lauryl ethersulfate (SLES) instead of sodium dodecylsulfate (SDS).

Formulation 9—same as Formulation 5, but with 2% alpha olefin sulfonate (AOS) instead of sodium dodecyl sulfate (SDS).

Formulation 10—same as Formulation 3, but with 0.2% Merquat Cationic (MQ100).

Formulation 11—same as Formulation 3 but with no Merquat Cationic (MQ100).

Formulation 12—same as Formulation 3, but with 1.5% castor oil (coated on the surface of the TiO$_2$ coated mica) and no MQ100.

Examples 1-24

In the Table below are found examples of bars with optical modifier structured in different ways.

| | | | | Delta | | |
|---|---|---|---|---|---|---|
| Examples | Formulation | Description | % Gloss | L | a | b |
| 1 | 1 | 60% talc | −7.9 | 0.3 | 0.1 | 0.0 |
| 2 | 1 | | 21.6 | −0.3 | −0.7 | −0.4 |
| 3 | 2 | | −45.1 | 20.3 | −1.4 | −4.0 |

-continued

| Examples | Formulation | Description | % Gloss | Delta L | a | b |
|---|---|---|---|---|---|---|
| 4 | 2 | | −44.6 | 27.5 | −1.8 | −7.2 |
| 5 | 3 | | −12.9 | 2.5 | 0.1 | −4.0 |
| 6 | 3 | | 0.0 | −0.7 | −1.1 | 15.0 |
| 7 | 4 | | 50.0 | 7.0 | −1.2 | −4.9 |
| 8 | 4 | | 93.6 | 10.4 | −1.3 | −5.3 |
| 9 | 5 | | 15.0 | 2.6 | −0.5 | −1.4 |
| 10 | 5 | | 74.7 | 8.6 | −1.3 | −3.8 |
| 11 | 6 | | 110.8 | 3.2 | −0.7 | −1.6 |
| 12 | 6 | | 81.9 | 1.5 | −1.1 | −1.9 |
| 13 | 7 | | 32.2 | 0.4 | −1.3 | −2.4 |
| 14 | 7 | | 19.2 | 2.8 | −0.7 | −1.2 |
| 15 | 8 | | 3.28 | 0.05 | −0.21 | −1.73 |
| 16 | 8 | | 12.25 | 0.79 | 0.44 | 0.76 |
| 17 | 9 | | 33.0 | 1.41 | −0.84 | −0.68 |
| 18 | 9 | | 56.6 | 1.13 | −0.81 | −1.63 |
| 19 | 10 | | 31.9 | 0.34 | −1 | −1.42 |
| 20 | 10 | | 57.3 | 1.4 | −0.57 | −1.58 |
| 21 | 11 | | 5 | −0.42 | 0.27 | 0.77 |
| 22 | 11 | | 5.7 | 0.66 | −0.14 | −0.97 |
| 23 | 12 | | 32.9 | 0.87 | −0.59 | −0.87 |
| 24 | 12 | | 20.6 | 1.19 | −0.37 | −0.46 |

A brief explanation of examples is indicated below:

From examples 3 to 14, the data shows that the new deposition system (cationic polymer/anionic surfactant) has significant amount of deposition that leads to large changes in visual appearance and attributes.

Examples 3, 4, 5, and 6 (sugar and PEG bars) have a high deposition of $TiO_2$ and have the ability to increase whiteness and opacity (hiding power) in a person's appearance.

Examples 7, 9, and 10 show an increase in reflectance and whiteness using titania coated mica. The effects are similar to examples 3 to 6, except now there is radiance.

Examples 11, 12, 13, and 14 (sugar and PEG bars), with BiOCl, have a large increase in reflectance/radiance with little increase in whiteness.

Examples 1 and 2 (85/15 bar with 60% talc), however, is a case of minimal/poor deposition. It shows minimal whitening and reflectance, even though it contains 60% talc. The other sugar and PEG bar examples have only 10% particle composition.

Examples 15 and 16 are sugar bars with titania coated mica with different surfactant (SLES). As compared to Examples 19, 20, 21, 22; these examples show lower/poor deposition and visual effect (reflectance).

Examples 17 and 18 are sugar bars with titania coated mica with another different surfactant (AOS). The deposition and visual/reflectance results are intermediate between those using SDS and SLES.

Examples 19 and 20 are sugar bars with titania coated mica with lower MQ 100 cationic polymer. There is a lower resulting reflectance/radiance and L values corresponding to lower deposition.

Examples 21 and 22 are sugar bars with titania coated mica with no MQ 100 cationic polymer. There is little to no visual change for the lack of any deposition.

Examples 23 and 24 are sugar bars with titania coated mica with 1.5% Castor oil (coated on the surface of the $TiO_2$ coated mica) and no MQ 100 cationic polymer. Even without the MQ100, there is intermediate amount of deposition and corresponding visual attributes (reflectance/radiance).

Examples 25, 26, and 27

The following soap bars were made and are discussed further below.

EXAMPLE 25

| Ingredient | % by wt. |
|---|---|
| Soap (85/15 tallow/palm kernel oil) | 52.51 |
| Sunflower oil | 10.40 |
| Sugar | 15.60 |
| Mica (Timiron MP-115) ® | 10.40 |
| Water | 9.53 |
| Perfume | 1.56 |

Example 26

EXAMPLE 26

| Ingredient | % by wt. |
|---|---|
| Soap (85/15 tallow/palm kernel oil) | 57.10 |
| Sunflower oil | 6.00 |
| Silicone (5000 Cs) | 6.00 |
| Glycerin | 6.00 |
| Mica (Timiron MP-115) ® | 10.00 |
| Water | 13.39 |
| Perfume, Minors | ~1.51 |

EXAMPLE 27

| Ingredient | % by wt. |
|---|---|
| Soap (85/15 tallow/palm kernel oil) | 68.15 |
| Glycerin | 1.50 |
| Sunflower oil | 4.00 |
| Mica (Timiron MP-115) ® | 4.98 |
| Glycerin Monostearate | 1.50 |
| Cationic (Merquat 100) | 3.40 |
| CTAC (cetyl trimethylammonium chloride) | 0.40 |
| Water | 14.55 |
| Perfume and other minors | ~1.56 |

Optical Effect

| | ΔL | | %Δ Gloss | |
|---|---|---|---|---|
| Example | Direct Contact | Lather Contact | Direct Contact | Lather Contact |
| 25 | 1.7 | 1.5 | 19 | 38 |
| 26 | 1.1 | 1.6 | 4 | 50 |
| 27 | 2.5 | 7.7 | 34 | 71 |

From Examples 25-27 above, several observations may be made.

Example 25 uses sunflower oil as an emollient although, by itself, it may not be an extremely efficient deposition aid. When silicon is added to be part of the deposition system (Example 26), it can be seen from gloss data that deposition is increasing (i.e., from % Δ gloss 38 to 50). Neither Examples 25 or 26 have cationic deposition polymer.

Finally, Example 27 shows that when both the deposition system has oil/emollient as part of the deposition system and there is cationic deposition polymer, then shine enhances significantly (% Δ gloss 71) even at lower oil levels (only 4% sunflower).

We claim:
1. A bar composition for delivery of enhanced visual benefits to the skin with specific optical attributes comprising:
   (a) from about 5% to about 75% by wt. surfactant;
   (b) from 0.1 to 35% by wt. of solid particulate optical modifier which exhibits a specific set of optical properties, defined by ΔL, Δa*, Δb*, change in reflectivity and/or change in opacity, and which, in combination with a deposition enhancement system, provides at least 5% change in at least one of said optical properties being targeted when said composition is applied to the skin;
   (c) from 0.1 to 25% by wt. of a deposition enhancement system, wherein, the deposition enhancement system comprises 0.1 to 10% of a cationic polymer or polymers having an average charge density about 6.2 Meq/gram; and 0.1 to 30% by wt. of an anionic surfactant which forms precipitate with said cationic polymer or polymers upon dilution; said anionic forming the precipitate being selected from the group consisting of $C_{10}$ to $C_{24}$ fatty acid soaps, sulfosuccinates, alkyl sulfates, and mixtures thereof and
   (d) from about 0.1% to 80% of a hydrophilic structural dispersant selected from the carom consisting of water soluble polyalkylene glycols having a molecular weight of 2000 to 500,000; polysaccharides; alkaloid derived polymers and mixtures thereof; and
   (e) 1% to 12% by wt. water,
   wherein the deposition enhancement system further comprises oil/emollient enveloping/surrounding said optical modifier; and/or comprises oil/emollient which forms an emulsion system in which optical modifiers are emulsified in the oil/emollient or are enveloped by the oil/emollient during dilution with water.

2. A composition according to claim 1 wherein the optical attribute affected by change of at least 5% in at least one of said optical properties is chosen from skin shine, skin lightness, skin color, skin glow, skin radiance, skin optical uniformity, skin evenness and mixtures thereof.

3. A composition according to claim 1, comprising 5% to 75% by wt. surfactant.

4. A composition according to claim 1 wherein the skin site wherein the delivery of optical benefits is targeted is skin plateaus and/or crevices on skin.

5. A composition according to claim 1, comprising 0.2% to 25% by wt. optical modifier.

6. A composition according to claim 1 providing changes in one or multiple attributes wherein delivery of modifier provides change in defined values and/or percentages as noted below:
   ΔL of from 0 to ±10 L units, wherein said L units are defined by Hunter Lab Color Meter;
   Δa* of from 0 to ±10 a* units, wherein said a* units are defined by Hunter Lab Color Meter;
   Δb* of from 0 to ±10 b* units, wherein said b* units are defined by Hunter Lab Color Meter;
   reflectance change of 0 to ±300% as defined by change in gloss measured from a gloss meter;
   opacity change of 0 to ±50% measured in opacity contrast and defined as ΔL divided by 60;
   wherein at least one of the values noted is a change of at least 5% from the initial value prior to delivery of modifier.

7. A composition according to claim 1 providing change in shine or glow wherein delivery of modifier provides change in defined values as noted below:
   ΔL of from 0 to ±10 L units, wherein said L units are defined by Hunter Lab Color Meter;
   change of reflectance of 0 to ±300% as defined by change in gloss measured by a gloss meter;
   change in opacity of 0 to ±20% measured in opacity contrast defined by ΔL divided by 60;
   wherein Δa* and Δb* are ≦2 units and wherein at least one of L, reflectance or opacity is a change of at least 5% from initial value prior to delivery of modifier.

8. A composition according to claim 1 providing change in lightening, whitening, and/or color wherein delivery of modifier provides change in defined values as noted below:
   ΔL of from 0 to ±10 L units, wherein L units are defined by Hunter Lab Color Meter;
   Δa* of from 0 to ±10 a* units, wherein a* units are defined by Hunter Lab Color Meter;
   Δb* of from 0 to ±10 b* units, wherein b* units are defined by Hunter Lab Color Meter;
   change in opacity of 0 to ±50% measured by opacity contrast, wherein said contrast is defined by ΔL divided by 60;
   wherein Δ reflectance is ≦10%, Δ reflectance being measured as change in gloss where gloss is measured in a gloss meter;
   wherein at least one of L, a*, b* or reflectance is a change of at least 5% from initial value prior to delivery of modifier.

9. A composition according to claim 1, providing change in skin optical uniformity, evenness, blurring and/or soft focus, wherein delivery of modifier provides change in defined value as noted below:
   ΔL of from 0 to ±5 units, wherein said L units are defined by Hunter Lab Color Meter; change in reflectance of 0 to ±100% which is defined in gloss units measured by a gloss meter; change in 0 to ±50%, measured in opacity contrast which is defined by ΔL divided by 60; wherein Δa* and Δb* are ≦2 units.

10. A composition according to claim 1, wherein a mixture of one or more desired visual attributes is obtained by varying ΔL, Δa*, Δb*, Δ reflectance and Δ opacity values to fit into areas defining one or more such attributes.

11. A composition according to claim 1, wherein said optical modifier is a non colored or colored organic or inorganic material selected from organic pigments; inorganic pigments; polymers and fillers in turn selected from: titanium dioxide; zinc oxide; colored iron oxide; chromium oxide, hydroxide or hydrate; alumina; silica; zirconia; barium sulfate; silicates; alkaloid polymers and derivatives thereof; polyalkylene; nylon; ultramarine; alkaline earth carbonate; talc; sericite; natural and synthetic mica; platy substrate coated with organic and inorganic materials; bismuth oxychloride; and mixtures thereof.

12. A composition according to claim 1, wherein said optical modifier is a UV sunscreen material with a $D_{50}$ <100 nanometers.

13. A composition according to claim 1, said optical modifier is defined as follows:
   (a) Exterior surface with refractive index of 1.3 to 4.0;
   (b) geometry which is spheroidal, platy or cylindrical;
   (c) $D_{50}$ of ≦200 microns in particle size; and
   (d) color which is obtained fluorescence color, absorption color and/or interference color.

14. A composition according, to claim 7 wherein the particulate optical modifier is further defined by:

(a) an exterior surface of refractive index 1.8 to 4.0,
(b) geometry which are platy or cylindrical;
(c) dimensions of spheroidal particles of 0.1 to 200 μm; dimensions of platy particles of 10 to 200 μm; and dimensions of cylindrical particles 10 to 200 μm in length and 0.5 to 5.0 μm in diameter; and
(d) $D_{50}$ of ≦200 microns in particle size.

15. A composition according to claim 8 wherein the particulate optical modifier is further defined by:
(a) an exterior surface of refractive index 1.3 to 4.0,
(b) geometry which are platy or spheroidal;
(c) diversions of spheroidal particles of 0.1 to 1 μm; and diversion of platy particles 1 to 30 μm;
(d) $D_{50}$ of ≦30 microns in particle size; and
(e) color by florescence, absorption and/or interference.

16. A composition according to claim 9 wherein the particulate optical modifier is further defined by:
(a) an exterior surface of refractive index 1.3 to 20;
(b) geometry which are spheroidal, platy, or cylindrical;
(c) dimensions of spheroidal particles of 0.1 to 200 μm; and dimension of platy particles 1 to 10 μm; dimension of cylindrical particles 1 to 10 μm in length and 0.5 to 5.0 μm in diameter; and
(d) $D_{50}$ of ≦200 microns in size.

17. A composition according to claim 1, wherein the precipitate is a floc which can be broken upon shear or rubbing to form a uniform and dispersed film on surface of skin.

18. A composition according to claim 1, additionally comprising about 0.1 to 30% by wt. of a granular anionic polymer which is a natural alkaloid polymer.

19. A composition according to claim 18, wherein said polymer is starch and derivatives, cellulose and derivatives and mixtures thereof.

20. A composition according to claim 11, wherein optical particles of interest contain a surface modification selected from amino acids, proteins, fatty acids, lipids, phospholipids, anionic and/or cationic oligomers/polymers and mixtures thereof.

21. A composition according to claim 1, wherein the particles are dispersed on the skin in that less than 30% of the particles have a size of 10 times or more than the $D_{50}$ particle size as measured by optical microscopy.

22. A composition according to claim 21, wherein said polymer is starch and derivatives, cellulose and derivatives and mixtures thereof.

23. A composition according to claim 11, wherein optical particles of interest contain a surface modification selected from amino acids, proteins, fatty acids, lipids, phospholipids, anionic and/or cationic oligomers/polymers and mixtures thereof.

24. A composition according to claim 1, wherein the particles are dispersed on the skin in that less than 30% of the particles have a size of 10 times or more than the $D_{50}$ particle size as measured by optical microscopy.

* * * * *